US00PP21563P2

(12) United States Plant Patent
Wain

(10) Patent No.: US PP21,563 P2
(45) Date of Patent: Dec. 7, 2010

(54) ***CHRYSANTHEMUM* PLANT NAMED 'YOENCINO'**

(50) Latin Name: *Chrysanthemum×morifolium*
Varietal Denomination: Yoencino

(75) Inventor: Peter Wain, Locks Heath (GB)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/587,023

(22) Filed: Oct. 1, 2009

(51) Int. Cl.
*A01H 5/00* (2006.01)

(52) U.S. Cl. ..... Plt./286

(58) Field of Classification Search ..... Plt./286
See application file for complete search history.

*Primary Examiner*—Susan B McCormick Ewoldt
(74) *Attorney, Agent, or Firm*—S. Matthew Edwards

(57) ABSTRACT

A new *Chrysanthemum* plant named 'Yoencino,' particularly distinguished by the medium sized anemone flower-type with spoon shaped bright greyed-red ray florets, good floriferousness, and small dark foliage.

1 Drawing Sheet

Latin name of the genus and species of the plant claimed: *Chrysanthemum×morifolium.*

Varietal denomination: 'Yoencino'.

BACKGROUND OF THE NEW PLANT

The present invention comprises a new *Chrysanthemum,* botanically known as *Chrysanthemum×morifolium,* and hereinafter referred to by the variety name 'Yoencino'.

'Yoencino' is a product of a planned breeding program. The new cultivar has medium sized anemone flower-type with spoon shaped bright greyed-red ray florets, good floriferousness, and small dark foliage.

'Yoencino' originated from a hybridization made in January 2004 in a controlled breeding environment in Fareham, Hampshire, United Kingdom. The female parent was the proprietary plant designated 'Cashmere,' unpatented, with anemone type flowers, medium short plant height and small to medium sized flowers.

The male parent of 'Yoencino' was an unpatented hybrid seedling identified as 'P865G 2' with spoon shaped, single gold flowers, and approximately a 54 day flowering response.

'Yoencino' was selected as one flowering plant within the progeny of the stated cross in the September 2004 in a controlled environment in Fareham, Hampshire, United Kingdom.

The first act of asexual reproduction of 'Yoencino' was accomplished when vegetative cuttings were propagated from the initial selection in September 2004 in a controlled environment in Fareham, Hampshire, United Kingdom.

A Plant Breeder's Right for this cultivar was applied for in Canada in October 2008. 'Yoencino' has not been made publicly available more than one year prior to the filing of this application.

BRIEF SUMMARY OF INVENTION

Horticultural examination of plants grown from cuttings of the plant initiated in September 2004 and continuing thereafter, has demonstrated that the combination of characteristics as herein disclosed for 'Yoencino' are firmly fixed and are retained through successive generations of asexual reproduction.

'Yoencino' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Chrysanthemum* as a new and distinct variety

BRIEF DESCRIPTION OF THE PHOTOGRAPHS

The accompanying photographic drawing shows typical flower and foliage characteristics of 'Yoencino' with colors being as true as possible with an illustration of this type. The photographic drawing shows four flowering potted plants of the new variety, growing in a five inch pot, and a close-up of the flowers.

DETAILED BOTANICAL DESCRIPTION

The plant descriptions, measurements and aforementioned photographs were taken in Gilroy, Calif. in April 2009 under greenhouse conditions. These plants were started and grown in central coastal California, then shipped to Gilroy in April 2009. Plants were grown under conditions which approximate those generally used in commercial potted *chrysanthemum* production and were about 9 weeks of age.

Color references are made to The Royal Horticultural Society Colour Chart (R.H.S.) 2001.

TABLE 1

DIFFERENCES BETWEEN THE NEW VARIETY 'YOENCINO' AND A SIMILAR VARIETY

| | 'Yoencino' | 'Yotobago' (U.S. Plant Pat. No. 15,412) |
|---|---|---|
| Flower type: | Anemone | Decorative |
| Flowering response time: | 48-53 days | 55 days |
| Flower size: | Larger | Smaller |
| Plant height: | Medium | Medium tall |

Plant:

*Form, growth and habit.*—Herbaceous pot-type; uniformly upright, strong and freely branching.

*Plant height.*—18-23 cm.

*Plant height* (*inflorescence included*).—25-31 cm.

*Plant width.*—15-17 cm.

Roots:

*Number of days to initiate roots.*—4 days at about 22 degrees C.

*Number of days to produce a rooted cutting.*—10 days at 22 degrees C.

*Type.*—Fine, fibrous, free branching.

*Color.*—RHS N155B but whiter.

Foliage:

*Arrangement.*—Alternate, simple.

*Immature, leaf color, upper surface.*—Closest to RHS 147A.

*Lower surface.*—Closest to RHS 146A but more green.

*Mature, leaf color, upper surface.*—Darker than RHS 147A.

*Lower surface.*—Closest to RHS 146A but more green.

*Length.*—6.8-8.5 cm.

*Width.*—3.6-4.8 cm.

*Shape.*—Ovate.

*Base shape.*—Attenuate.

*Apex shape.*—Mucronulate to abruptly acute.

*Margin.*—Palmately lobed, somewhat serrate.

*Texture, upper surface.*—Bi-fid T-shaped hairs.

*Lower surface.*—Bi-fid T-shaped hairs.

*Color of veins, upper surface.*—RHS 146B.

*Color of veins, lower surface.*—RHS 146B.

*Petiole color.*—RHS 146B.

*Length.*—1-1.3 cm.

*Diameter.*—0.3 cm.

*Texture.*—Bi-fid T-shaped hairs.

Stem:

*Quantity of main branches per plant.*—3-4.

*Quantity of leaves per branch.*—8-12.

*Color of stem.*—RHS 146A, but appears lighter because of the hairs.

*Length of stem.*—18-21 cm.

*Diameter.*—0.3-0.4 cm.

*Length of internodes.*—1.5-3.0 cm.

*Texture.*—Bi-fid T-shaped hairs.

*Color of peduncle.*—RHS 146A but appears lighter because hairs.

*Length of peduncle.*—3.8-5.0 cm.

*Peduncle diameter.*—0.15-0.2 cm.

*Texture.*—Bi-fid T-shaped hairs.

Inflorescence:

*Type.*—Composite type, solitary inflorescence (decorative, spoon-anenome-type) borne terminally above foliage, ray florets arranged acropetally on a capitulum. Many of the ray florets flatten out when they mature.

*Quantity of inflorescences per plant.*—8-10.

*Lastingness of individual blooms on the plant.*—15-20 days.

*Fragrance.*—Moderate.

Bud: (Just before opening/showing color):

*Color.*—RHS 162A.

*Length.*—1.0-1.3 cm.

*Width.*—1.1-1.4 cm.

*Shape.*—Oblate.

Immature inflorescence:

*Diameter.*—3.5-5.0 cm.

*Color of ray florets, upper surface.*—RHS 172B.

*Lower surface.*—Closest to RHS 164C.

Mature inflorescence:

*Diameter.*—6.0-6.4 cm.

*Total diameter of 'disc'.*—2.5-3.0 cm.

Ray florets:

*Average quantity of florets.*—57-60.

*Color of florets, upper surface.*—RHS 178B to RHS 178C with RHS 178A to RHS 178B at apex.

*Lower surface.*—Closest to RHS 164C with hint of RHS 172B at apex.

*Length.*—2.4-3.2 cm.

*Width.*—0.4-0.6 cm.

*Shape.*—Spoon shape; basal portion of margins are rolled inward and fused forming a short tube, leaving upper portion flat and open.

*Apex shape.*—Praemorse.

*Margin.*—Entire.

*Texture, upper surface.*—Papillose.

*Lower surface.*—Papillose.

Disc florets:

*Average quantity of florets.*—150-175.

*Color of florets.*—RHS 5A.

*Length.*—1-1.2 cm.

*Width.*—0.2-0.25 cm.

*Shape.*—Tubular, elongated.

*Apex shape.*—Acute, 5 pointed.

Phyllaries:

*Quantity.*—15-20.

*Color, upper surface.*—RHS 138A but appears lighter due to hairs.

*Lower surface.*—RHS 138A.

*Length.*—0.3 cm.

*Width.*—0.2 cm.

*Shape.*—Lanceolate.

*Apex shape.*—Acute.

*Based.*—Fused.

*Margins.*—Entire.

*Texture, upper surface.*—Glossy and smooth.

*Lower surface.*—Bi-fid T-shaped hairs.

Reproductive organs:

*Pistil.*—1.

*Length.*—0.7-0.8 cm.

*Style color.*—RHS 1B, but appears more translucent.

*Style length.*—0.45 cm.

*Stigma color.*—RHS 1C.

*Stigma shape.*—Bi-parted.

*Stamens.*—4.

*Color of filaments.*—RHS 1C.

*Length filaments.*—0.3 cm.

*Anther color.*—RHS 13B.

*Anther length.*—0.2 cm.

*Anther shape.*—Oblong.

*Color of pollen.*—RHS 17B.

*Pollen amount.*—Abundant.

*Fertility/seed set.*—Has not been observed on this hybrid.

Disease/pest resistance: Disease resistance or susceptibility has not been observed on this hybrid.

What is claimed is:

1. A new and distinct variety of *Chrysanthemum* plant named 'Yoencino,' substantially as illustrated and described herein.

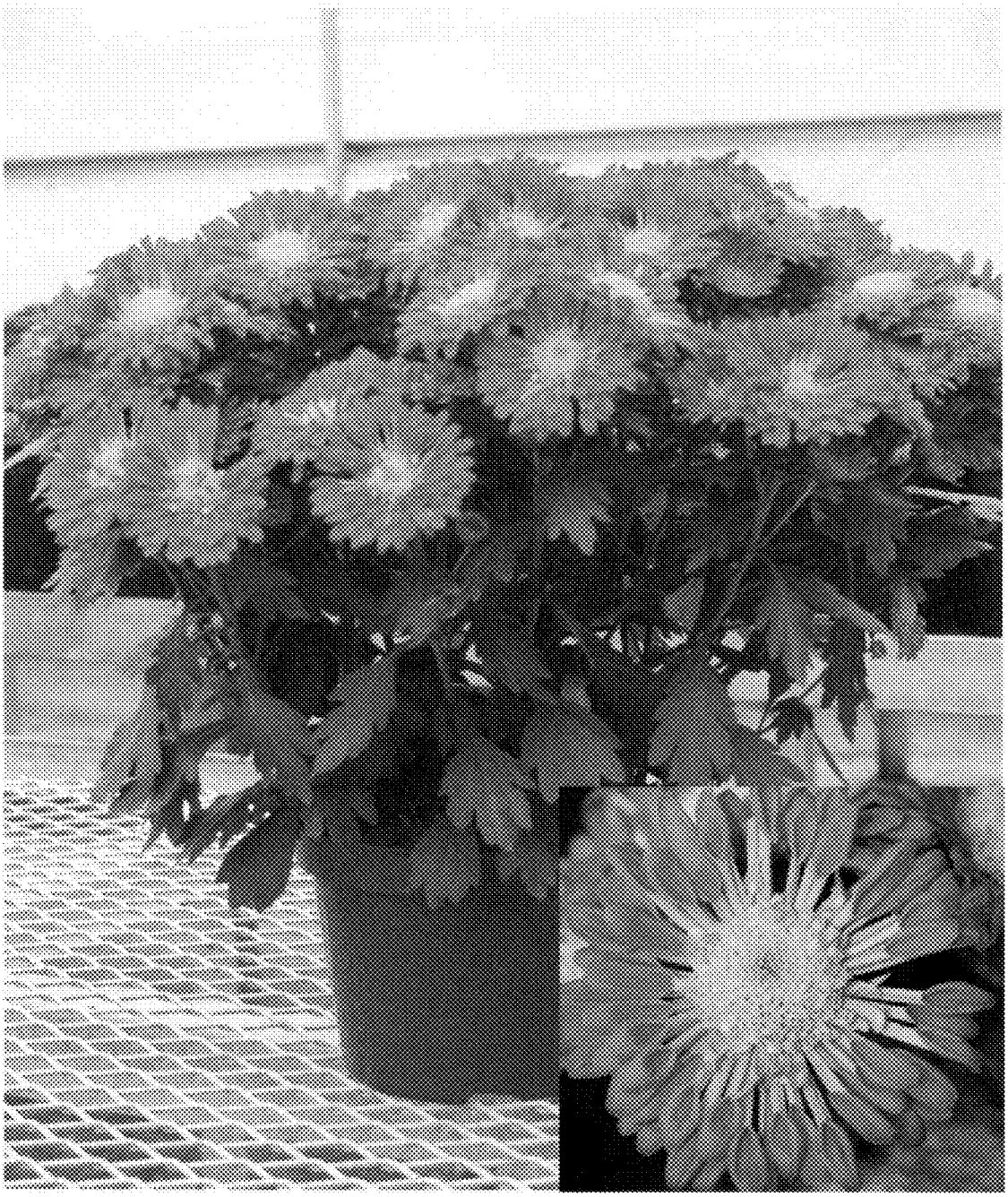

* * * * *